(12) United States Patent
Peyman

(10) Patent No.: US 12,023,471 B1
(45) Date of Patent: Jul. 2, 2024

(54) PLUNGERLESS ASPIRATION AND/OR INJECTION DEVICE AND METHOD USING THE SAME

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 18/229,970

(22) Filed: Aug. 3, 2023

Related U.S. Application Data

(63) Continuation-in-part of application No. 17/144,075, filed on Jan. 7, 2021, now Pat. No. 11,730,890.

(60) Provisional application No. 62/958,101, filed on Jan. 7, 2020.

(51) Int. Cl.
| | | |
|---|---|---|
| A61M 5/178 | (2006.01) | |
| A61B 10/00 | (2006.01) | |
| A61M 5/28 | (2006.01) | |
| A61M 5/31 | (2006.01) | |

(52) U.S. Cl.
CPC ..... *A61M 5/282* (2013.01); *A61M 2005/3112* (2013.01)

(58) Field of Classification Search
CPC .... A61M 5/282; A61M 5/3273; A61M 5/422; A61M 5/2425; A61M 2005/3265; A61M 5/3267
See application file for complete search history.

(56) References Cited

U.S. PATENT DOCUMENTS

| | | | |
|---|---|---|---|
| 1,668,588 A | * | 5/1928 | Greeley ............... A61M 5/282 604/212 |
| 2,618,263 A | | 11/1952 | Lakso et al. |
| 2,771,879 A | | 11/1956 | Salisbury |
| 3,776,238 A | | 12/1973 | Peyman et al. |
| 4,428,748 A | | 1/1984 | Peyman et al. |

(Continued)

FOREIGN PATENT DOCUMENTS

| | | | | |
|---|---|---|---|---|
| CH | 706928 A2 | * | 3/2014 | ............ A61M 5/42 |
| DE | 19537271 A1 | | 4/1997 | |
| DE | 10032937 A1 | | 1/2001 | |

OTHER PUBLICATIONS

Machine Translation of CH 7806928 A2 Marti (Year: 2014).*

(Continued)

*Primary Examiner* — Laura A Bouchelle
(74) *Attorney, Agent, or Firm* — The Law Office of Patrick F. O'Reilly III, LLC

(57) ABSTRACT

A plungerless aspiration and/or injection device and a method of using the same are disclosed herein. The plungerless aspiration and/or injection device includes a housing with an end portion extending outwardly from the housing, the end portion having an outer edge; a needle portion disposed in the housing, the needle portion including a needle tip, and the needle tip configured to be extended beyond the outer edge of the end portion of the housing; and a bulb portion disposed in the housing, the bulb portion defining a fluid containing cavity that is fluidly coupled to the needle portion, and the bulb portion being elastically deformable to perform aspiration, injection, and/or implantation on a patient. The outer edge of the end portion of the housing is configured to be pressed against a body portion of the patient prior to insertion of the needle tip so as to reduce a pain sensation.

20 Claims, 7 Drawing Sheets

(56) References Cited

U.S. PATENT DOCUMENTS

| | | |
|---|---|---|
| 4,548,601 A | 10/1985 | Lary |
| 4,955,871 A | 9/1990 | Thomas |
| 5,217,480 A | 6/1993 | Haber et al. |
| 5,487,725 A | 1/1996 | Peyman |
| 5,547,473 A | 8/1996 | Peyman |
| 6,432,078 B1 | 8/2002 | Peyman |
| 8,597,257 B2 * | 12/2013 | Modi ................. A61M 5/288 604/110 |
| 10,022,457 B2 | 7/2018 | Peyman |
| 2005/0101967 A1 | 5/2005 | Weber et al. |
| 2005/0251105 A1 | 11/2005 | Peyman |
| 2009/0171311 A1 | 7/2009 | Genosar et al. |
| 2010/0047914 A1 | 2/2010 | Peyman et al. |
| 2012/0265149 A1 | 10/2012 | Lerner |
| 2013/0018326 A1 * | 1/2013 | Hooven ............ A61M 5/14248 604/198 |
| 2013/0345669 A1 | 12/2013 | Ferreri et al. |
| 2021/0244884 A1 * | 8/2021 | Schabbach .......... A61M 5/2425 |

OTHER PUBLICATIONS

Peyman et al., "Subretinal semiconductor microphotodiode array", Ophthalmic Surgery and Lasers, Thorofare vol. 29, Iss. 3, (Mar. 1998): pp. 234-241.
Notice of Allowance in U.S. Appl. No. 17/144,075, dated Apr. 3, 2023.

* cited by examiner

PLUNGERLESS ASPIRATION AND/OR INJECTION DEVICE AND METHOD USING THE SAME

CROSS-REFERENCE TO RELATED APPLICATIONS

This patent application is a continuation-in-part of U.S. Nonprovisional patent application Ser. No. 17/144,075, entitled "Plungerless Aspiration And/Or Injection Device And Method Using The Same", filed on Jan. 7, 2021; and U.S. Nonprovisional patent application Ser. No. 17/144,075 claims priority to U.S. Provisional Patent Application No. 62/958,101, entitled "Plungerless Aspiration And Injection Device And Method Using The Same", filed on Jan. 7, 2020, the disclosure of each of which is hereby incorporated by reference as if set forth in their entirety herein.

STATEMENT REGARDING FEDERALLY SPONSORED RESEARCH OR DEVELOPMENT

Not Applicable.

Names of the Parties to a Joint Research Agreement

Not Applicable.

Incorporation by Reference of Material Submitted on a Compact Disk

Not Applicable.

BACKGROUND OF THE INVENTION

1. Field of the Invention

The invention generally relates to a plungerless aspiration and/or injection device and a method using the same. More particularly, the invention relates to a plungerless aspiration and/or injection device for aspirating a liquid biopsy or injecting a medication in bodily tissue.

2. Background

Despite progress in blood liquid biopsy, the aqueous and vitreous fluid is seldom used for diagnostic purposes except in cases of endophthalmitis. However, the aqueous, vitreous, and subretinal fluid contains many molecules that could provide information about the health of the retina, choroid, optic nerve, or the health of the lens or the trabecular meshwork of the eye.

At present, most medications are delivered to the eye by topical drops, or injection using known standard syringes. The topical application has the disadvantage of being washed from the surface of the eye rapidly by the flow of the tear film. The injected medication stays in the tissue a longer time. The syringes have been long used for either injection of medication or aspiration of fluid including a liquid biopsy from the eye or the veins, arteries, or body cavities.

The syringe is composed of a circular tubular body in which a plunger moves forward by the thumb of the user or the plunger is withdrawn using thumb and index fingers. A needle is placed on the syringe to penetrate tissue and deliver medication. The needle can be mounted on the syringe or turned in or out via a luer lock to the syringe.

The plunger also can be connected to an automated air pressure capsule for injection of mediation only. When activated, it forces the tip of the needle and medication, thereby injecting the medication in the tissue.

The use of a syringe for injection is in general cumbersome. It is hard to control the degree of the needle penetration in the tissue with the thumb, and aspiration requires the use of both hands to have the syringe stable in place. While one can predetermine the length of the needle that enters a cavity, it is still difficult to withdraw fluid without the use of both hands, one for stabilizing the syringe and another for withdrawing a liquid biopsy.

In general, the automated systems of injection for withdrawing fluid work like "one size fits all", but fall short in practice.

Therefore, there is a need for a plungerless aspiration and/or injection device for facilitating the aspiration of a liquid biopsy or the injection of a medication in bodily tissue. In addition, because of the sensitive structure of the eye, there is a need for a more refined aspiration of the liquid biopsy or injection of the medication in a corneal pocket created during refractive surgery, or in the small anterior chamber, under the conjunctiva, in the suprachoroidal space, or for the sub-retinal injection of a very small volume of medication.

BRIEF SUMMARY OF EMBODIMENTS OF THE INVENTION

Accordingly, the present invention is directed to a plungerless aspiration and/or injection device and a method using the same that substantially obviates one or more problems resulting from the limitations and deficiencies of the related art.

In accordance with one or more embodiments of the present invention, there is provided a plungerless aspiration and/or injection device that includes a housing; a needle portion disposed in the housing, the needle portion configured to be selectively retracted and extended by a user, the needle potion comprising a needle tip configured to be inserted into tissue of a patient for aspiration, injection, and/or implantation; and a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion.

In a further embodiment of the present invention, the plungerless aspiration and/or injection device further comprises a knob for manipulating the needle portion, the knob being slidably disposed within a slot of the housing. In this further embodiment, when the knob is moved in a first direction by the user, the needle portion is retracted into the housing; and, when the knob is moved in a second direction by the user, the needle portion is extended out of the housing, the second direction being opposite to the first direction.

In yet a further embodiment, the bulb portion is connected to the needle portion such that the bulb portion is displaced with the needle portion when the knob is moved in the first direction or second direction by the user.

In still a further embodiment, the housing comprises elastically deformable forked blades disposed over the bulb, the elastically deformable forked blades configured to be depressed by the user between a thumb and index finger of the user so as to more controllably regulate a flow of fluid out of, or into the needle tip.

In yet a further embodiment, the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

In still a further embodiment, the needle portion has a 19 gauge to 44 gauge needle In yet a further embodiment, the needle portion has a diameter between approximately 0.001 millimeters and approximately 2.0 millimeters, or more than 2.0 millimeters.

In still a further embodiment, the needle portion has a needle length between approximately 1 millimeters and approximately 100 millimeters, or more than 100 millimeters.

In yet a further embodiment, the bulb portion is formed from a compressible silicone, rubber, or other elastic polymer.

In still a further embodiment, the housing comprises a dull tip end so that, when the needle portion is retracted in the housing, the plungerless aspiration and/or injection device is able to be moved over a surface of the tissue of the patient to select a desired penetration location without scratching or cutting the surface of the tissue.

In yet a further embodiment, the housing comprises a graded flexible guard that indicates the amount of the fluid or medication that is injected in a body cavity.

In accordance with one or more other embodiments of the present invention, there is provided a method of using a plungerless aspiration and/or injection device. The method comprises the steps of: (i) providing a plungerless aspiration and/or injection device that includes a housing; a needle portion disposed in the housing, the needle portion configured to be selectively retracted and extended by a user, the needle potion comprising a needle tip configured to be inserted into tissue of a patient for aspiration, injection, and/or implantation; and a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion; (ii) positioning the housing of the plungerless aspiration and/or injection device over a body portion of the patient; (iii) displacing the needle portion of the plungerless aspiration and/or injection device outward from the housing such that the needle tip penetrates the tissue of the patient; and (iv) compressing the bulb portion of the plungerless aspiration and/or injection device to either inject a fluid or implant into the tissue of the patient, or to aspirate a fluid biopsy from a body cavity or the tissue of the patient.

In a further embodiment of the present invention, the method further comprises the step of filling the fluid containing cavity of the bulb portion with a fluid, a medication, an implant, proteins, cells, or genetic components; and the step of compressing the bulb portion further comprises compressing the bulb portion to inject the fluid, the medication, the implant, the proteins, the cells, or the genetic components into the tissue, circulation, or body cavity of the patient.

In yet a further embodiment, the step of filling the fluid containing cavity of the bulb portion further comprises filling the fluid containing cavity with pluralities of functionalized antibody-coated nanoparticles conjugated with checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs to be injected inside a tumor or circulation of the patient so as to release checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs. The checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs may also be provided in a flexible or rigid implant that is injected inside the eye, retina, cornea, choroid, a tumor or circulation of the patient, intramuscularly, subcutaneously, or under the mucosa. In addition, any medication may be provided in suspension in a solution or a solvent such as semifluorinated alkane, or perfluorocarbon liquids and administered by injection, as drops, or a spray.

In still a further embodiment, the checkpoint inhibitors, oncolytic viruses, viral-like particles, immune stimulators, and/or venoms conjugated with the functionalized antibody-coated nanoparticles are released in response to application of external energy, the external energy selected from the group consisting of laser, alternating magnetic field, a focused ultrasound, microwaves, and/or combinations thereof. In one embodiment, the medication is a photosensitizer, such as riboflavin or methylene blue, etc.

In yet a further embodiment, the step of filling the fluid containing cavity of the bulb portion further comprises filling the fluid containing cavity with an emulsion containing nanoparticles or microparticles, solid lipid particles, gold magnetic nanoparticles or microparticles, gold non-magnetic nanoparticles or microparticles, liposomes, micelles, and/or dendrimers in a fluid. In this further embodiment, the microparticles may be up to the size of one millimeter or more.

In still a further embodiment, the step of filling the fluid containing cavity of the bulb portion further comprises filling the fluid containing cavity with a viscoelastic material containing a medication and/or a photosensitizer that is activated using ultraviolet radiation or another type of radiation to crosslink proteins in the tissue of the patient.

In yet a further embodiment, the photosensitizer is selected from the group consisting of riboflavin, porphyrin derivatives, indium, platinum, rhodium plus albumin, eosin, rose Bengal, phthalocyanines, carotenoids, and/or combinations thereof.

In still a further embodiment, the step of filling the fluid containing cavity of the bulb portion further comprises filling the fluid containing cavity with predetermined non-toxic doses of a medication selected from the group consisting of antibiotics, antivirals, anti-parasites, anti-fungals, antivirals, low molecular weight heparin, hyaluronic acid, and/or combinations thereof in a solution or emulsion of nanoparticles or microparticles for slow release of the medication. In this further embodiment, the plungerless aspiration and/or injection device is disposable.

In yet a further embodiment, the step of compressing the bulb portion further comprises compressing the bulb portion to aspirate the fluid biopsy from the body cavity or the tissue of the patient for subsequent analysis.

In still a further embodiment, the method further comprises the step of creating a small hole in an outer wall of the bulb portion to aspirate the fluid biopsy from the body cavity or the tissue of the patient through the needle portion, to the bulb portion, and then to outside the plungerless aspiration and/or injection device where the fluid biopsy is collected, so that the plungerless aspiration and/or injection device is able to be used as a passive biopsy collection system, or the bulb can be filled with a medication, e.g., initially filled or the medication injected in it with a fine needle which is self-sealing for active administration of the medication or withdrawal.

In yet a further embodiment, the plungerless aspiration and/or injection device is configured for a single use on a patient; and the method further comprises the step of disposing of the plungerless aspiration and/or injection device after injecting the fluid or an implant into the tissue of the patient, or aspirating the fluid biopsy from the body cavity or the tissue of the patient.

In still a further embodiment, the method further comprises the steps of inserting the needle tip of the needle portion of the plungerless aspiration and/or injection device inside corneal tissue after femtosecond laser application or a Small Incision Lenticule Extraction procedure; and displacing the needle tip of the needle portion inside the corneal tissue so as to dissect bridges of the corneal tissue after the femtosecond laser application or the Small Incision Lenticule Extraction procedure.

In accordance with yet one or more other embodiments of the present invention, there is provided a plungerless aspiration and/or injection device that includes a housing, the housing including an end portion extending outwardly from the housing, the end portion having an outer edge that is configured to be pressed against a body portion of a patient; a needle portion disposed in the housing, the needle portion including a needle tip, and the needle tip configured to be extended beyond the outer edge of the end portion of the housing; and a bulb portion disposed in the housing, the bulb portion defining a fluid containing cavity that is fluidly coupled to the needle portion, and the bulb portion being elastically deformable so that the user is able to perform aspiration, injection, and/or implantation on the patient by manipulating the bulb portion. In these one or more other embodiments, the outer edge of the end portion of the housing is configured to be pressed against the body portion of the patient prior to insertion of the needle tip of the needle portion into the body portion of the patient so as to reduce a pain sensation of the patient resulting from the insertion of the needle tip of the needle portion.

In a further embodiment of the present invention, the end portion of the housing is an inverted conical end portion or inverted frustoconical end portion.

In yet a further embodiment, the housing comprises elastically deformable forked blades disposed over the bulb, the elastically deformable forked blades configured to be depressed by the user between a thumb and index finger of the user so as to more controllably regulate a flow of fluid out of, or into the needle tip.

In still a further embodiment, the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

In yet a further embodiment, the needle portion has a 19 gauge to 44 gauge needle In still a further embodiment, the needle portion has a diameter between approximately 0.001 millimeters and approximately 1.0 millimeters.

In yet a further embodiment, the needle portion has a needle length between approximately 1 millimeters and approximately 100 millimeters.

In still a further embodiment, the bulb portion is formed from a compressible silicone, rubber, or other elastic polymer.

In yet a further embodiment, the housing comprises a graded flexible guard that indicates the amount of the fluid or medication that is injected in a body cavity.

In accordance with one or more other embodiments of the present invention, there is provided a method of using a plungerless aspiration and/or injection device. The method comprises the steps of: (i) providing a plungerless aspiration and/or injection device that includes a housing, the housing including an end portion extending outwardly from the housing, the end portion having an outer edge that is configured to be pressed against a body portion of a patient; a needle portion disposed in the housing, the needle portion including a needle tip, and the needle tip configured to be extended beyond the outer edge of the end portion of the housing; and a bulb portion disposed in the housing, the bulb portion defining a fluid containing cavity that is fluidly coupled to the needle portion, and the bulb portion being elastically deformable so that the user is able to perform aspiration, injection, and/or implantation on the patient by manipulating the bulb portion; (ii) pressing the outer edge of the end portion of the housing against the body portion of the patient prior to insertion of the needle tip of the needle portion into the body portion of the patient so as to reduce a pain sensation of the patient resulting from the insertion of the needle tip of the needle portion; and (iii) compressing the bulb portion of the plungerless aspiration and/or injection device to either inject a fluid or implant into the tissue of the patient, or to aspirate a fluid biopsy from a body cavity or the tissue of the patient.

In a further embodiment of the present invention, the end portion of the housing is an inverted conical end portion or inverted frustoconical end portion; and the step of pressing the outer edge of the end portion of the housing against the body portion of the patient further comprises pressing the outer edge of the inverted conical end portion or inverted frustoconical end portion of the housing against the skin of the patient to numb the subcutaneous nerves prior to insertion of the needle tip of the needle portion into the skin of the patient so as to reduce a pain sensation of the patient resulting from the insertion of the needle tip of the needle portion.

In yet a further embodiment, the method further comprising the step of filling the fluid containing cavity of the bulb portion with a vaccine and/or one or more antivirals, antibiotics, antifungals, or antineoplastic medications, the vaccine made from dead viruses, bacteria, fungi, parasites, or tumor cells; and the step of compressing the bulb portion further comprises compressing the bulb portion to inject the vaccine and/or one or more antivirals, antibiotics, antifungals, or antineoplastic medications into the tissue, circulation, or body cavity of the patient.

In still a further embodiment, the method further comprises the step of filling the fluid containing cavity of the bulb portion with non-toxic dark nanoparticles or microparticles; and the step of compressing the bulb portion further comprises compressing the bulb portion to inject the non-toxic dark nanoparticles or microparticles inside a desired part of a central cornea of the patient so as to create a 1-3 mm diameter darkened annular area, while leaving a 1-2 mm diameter central transparent area for light to pass through the central transparent area, which functions as a pinhole to treat presbyopia, myopia, and reduce astigmatic aberrations of the cornea.

In yet a further embodiment, the method further comprises the step of filling the fluid containing cavity of the bulb portion with a viscoelastic material and a flexible intraocular lens that is able to be pressed through the needle tip of the plungerless aspiration and/or injection device when injected; and the step of compressing the bulb portion further comprises compressing the bulb portion to inject the flexible intraocular lens into a lens capsule of an eye of the patient after removal of a cataract from inside the lens capsule.

In still a further embodiment, the method further comprises the step of filling the fluid containing cavity of the bulb portion with a viscoelastic material and a flexible intracorneal inlay that is able to be pressed through the needle tip of the plungerless aspiration and/or injection device when injected; and the step of compressing the bulb portion further comprises compressing the bulb portion to inject the flexible intracorneal inlay into a corneal cavity in a cornea of an eye of the patient after the corneal cavity has been prepared using a femtosecond laser.

In yet a further embodiment, the method further comprises the step of filling the fluid containing cavity of the bulb portion with piezoelectric nanoparticles or piezoelectric microparticles; and the step of compressing the bulb portion further comprises compressing the bulb portion to inject the piezoelectric nanoparticles or piezoelectric microparticles in the vitreous cavity to migrate into a retina of an eye of the patient or directly into the retina or subretinal space so that the piezoelectric nanoparticles or piezoelectric microparticles are able to be stimulated with ultrasound from outside the eye of the patient.

In still a further embodiment, the method further comprises the step of filling the fluid containing cavity of the bulb portion with nanoparticles or microparticles operating as carriers of gene-CRISPR/cas9 complexes; and the step of compressing the bulb portion further comprises compressing the bulb portion to inject the nanoparticles or microparticles and the gene-CRISPR/cas9 complexes in the vitreous cavity or the subretinal space to migrate into a retina of an eye of the patient or directly into the retina so that the nanoparticles or microparticles are able to be stimulated with light or ultrasound from outside the eye of the patient to enhance gene delivery after the light or ultrasound stimulation, thereby inducing an electrical cell membrane polarization or depolarization, which opens the cell membrane pores permitting genes or the gene-CRISPR/cas9 complexes to enter cell cytoplasms in the macular area of the retina and target mutated DNA, cut to remove the mutated DNA, and/or replace the mutated DNA with an unmutated DNA segment.

In yet a further embodiment, the method further comprises the step of filling the fluid containing cavity of the bulb portion with progenitor nerve stem cells or mesenchymal cells; and the step of compressing the bulb portion further comprises compressing the bulb portion to inject the progenitor nerve stem cells or mesenchymal cells into an eye of the patent so that the progenitor nerve stem cells or mesenchymal cells migrate under a retina of the eye to a central foveal area through retinal intercellular space, and replace retinal cells damaged by age-related macular degeneration or retinitis pigmentosa.

In still a further embodiment, the plungerless aspiration and/or injection device is configured for a single use on a patient; and the method further comprises the step of disposing of the plungerless aspiration and/or injection device after injecting the fluid or implant into the tissue of the patient, or aspirating the fluid biopsy from the body cavity or the tissue of the patient for chemical or cellular analysis.

In yet a further embodiment, the method further comprises the steps of inserting the needle tip of the needle portion of the plungerless aspiration and/or injection device inside corneal tissue after femtosecond laser application, a Small Incision Lenticule Extraction procedure, or corneal inlay implantation; and displacing the needle tip of the needle portion inside the corneal tissue so as to dissect bridges of the corneal tissue after the femtosecond laser application, the Small Incision Lenticule Extraction procedure, or corneal inlay implantation.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same elements are always denoted using the same reference characters so that, as a general rule, they will only be described once.

DETAILED DESCRIPTION OF EMBODIMENTS OF THE INVENTION

In one embodiment, there is a need for a simplified system that can be easily controlled by thumb and index fingers for injection of fluid or implantation of small sized implants, for example, drug delivery of polymeric nano- and microparticulates or injecting a medication in solution or as emulsion or withdrawing a precise amount of fluid without moving the instrument that could damage the wall of the cavity, such as an artery or vein or the wall of the body cavity, such as the anterior chamber damaging the cornea, lens, or the iris of the eye and/or the vitreous cavity without damaging the retina, etc. (refer to FIGS. 1A-3H).

In one embodiment, the instrument 10 is composed of a housing where its front end covers a movable needle 12 and its back is like a flexible fork 20 or spatula-like extension covering an elongated semi-elastic compressible, silicone bulb reservoir 18 made of silicone or the like, rubber, or elastic polymer (see FIGS. 1A-1E).

Figure 1A:
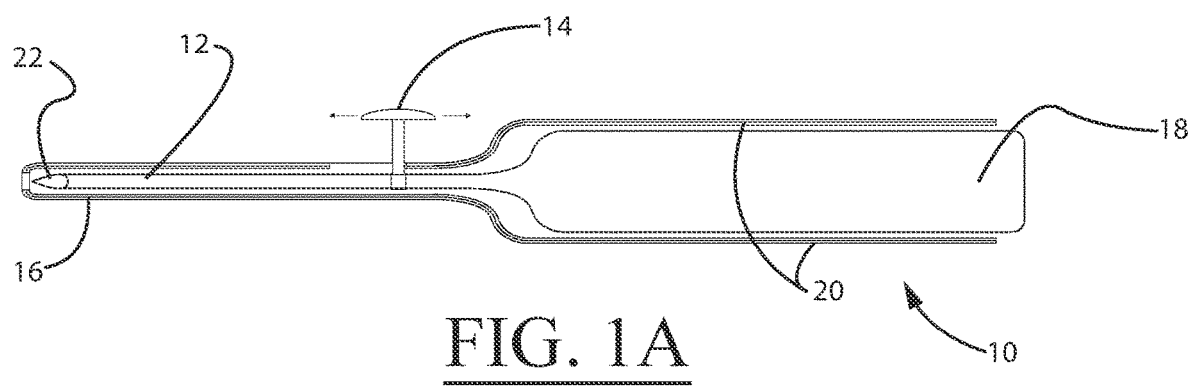
FIG. 1A is a side cross-sectional view of a plungerless aspiration and/or injection device, according to an illustrative embodiment of the invention, wherein the needle of the device is in a retracted position.
Figure 1B:
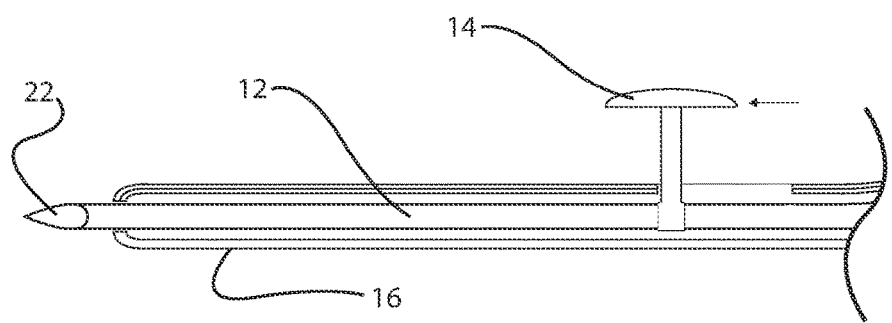
FIG. 1B is a partial side cross-sectional view of a distal end of the plungerless aspiration and/or injection device of FIG. 1A, wherein the needle of the device is in an extended, exposed position.
Figure 1C:
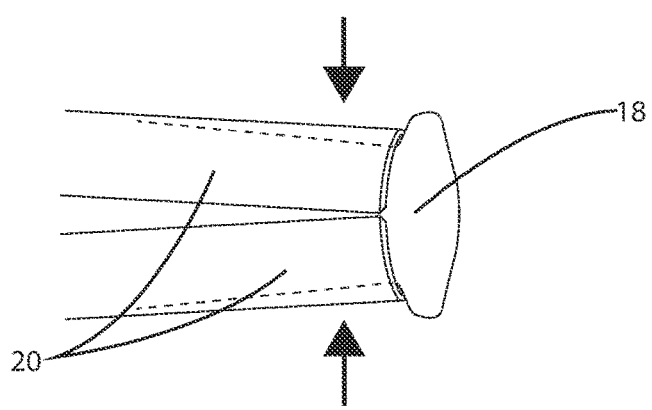
FIG. 1C is a partial side cross-sectional view of a proximal end of the plungerless aspiration and/or injection device of FIG. 1A, wherein the bulb and the fork of the device are illustrated in a compressed state.

In particular, as shown in the illustrative embodiment of FIGS. 1A-1C, the plungerless aspiration and/or injection device 10 comprises a housing 16; a needle portion 12 disposed in the housing 16, the needle portion 12 configured to be selectively retracted and extended by a user, the needle portion 12 comprising a needle tip 22 configured to be inserted into tissue of a patient for aspiration, injection, and/or implantation; and a bulb portion 18 disposed in the housing 16, the bulb portion 18 defining a fluid containing cavity that is fluidly coupled to the needle portion 12, and the bulb portion 18 being elastically deformable so that the user is able to perform the aspiration, the injection, and/or the implantation on the patient by manipulating the bulb portion 18.

Referring again to FIGS. 1A-1C, it can be seen that, in the illustrative embodiment, the plungerless aspiration and/or injection device 10 further comprising a knob 14 for manipulating the needle portion 12, the knob 14 being slidably disposed within a slot of the housing 16. When the knob 14 is moved in a first direction by the user, the needle portion 12 is retracted into the housing 16. Conversely, when the knob 14 is moved in a second, opposite direction by the user, the needle portion 12 is extended out of the housing 16. In the illustrative embodiment, the bulb portion 18 is connected to the needle portion 12 such that the bulb portion 18 is displaced with the needle portion 12 when the knob 14 is moved in the first direction or second direction by the user.

In the illustrative embodiment, as best shown in FIG. 1C, the housing 16 comprises elastically deformable forked blades 20 disposed over the bulb 18, the elastically deformable forked blades 20 configured to be depressed by the user between a thumb and index finger of the user so as to more controllably regulate a flow of fluid out of, or into the needle tip 22. The forked blades 20 may be spring-loaded to return to their undepressed state after being depressed by the user.

Figure 2A:
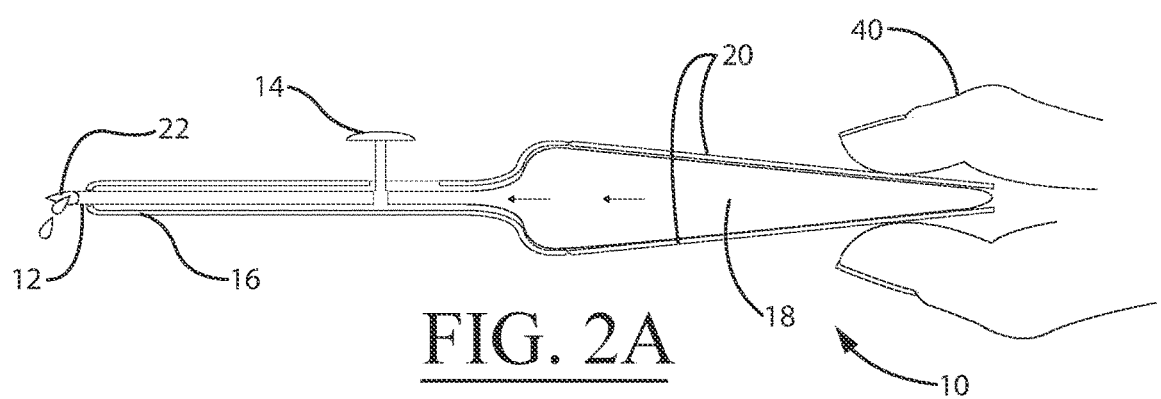
FIG. 2A is a side cross-sectional view of a plungerless aspiration and/or injection device, according to an illustrative embodiment of the invention, wherein the manner in which the device is used for injection is illustrated.
Figure 2B:
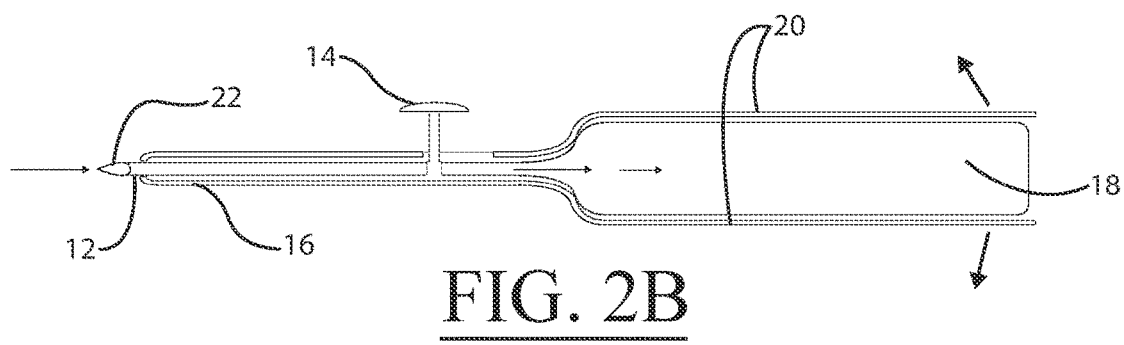
FIG. 2B is another side cross-sectional view of the plungerless aspiration and/or injection device of FIG. 2A, wherein the manner in which the device is used for aspiration is illustrated.

In FIG. 2A, the forked blades 20 of the illustrative plungerless aspiration and/or injection device 10 are shown being compressed by fingers of a user during injection of a fluid disposed in the bulb portion 18 of the device. In FIG. 2B, the forked blades 20 of the illustrative plungerless aspiration and/or injection device 10 are shown being displaced outwardly during aspiration.

Figure 2C:
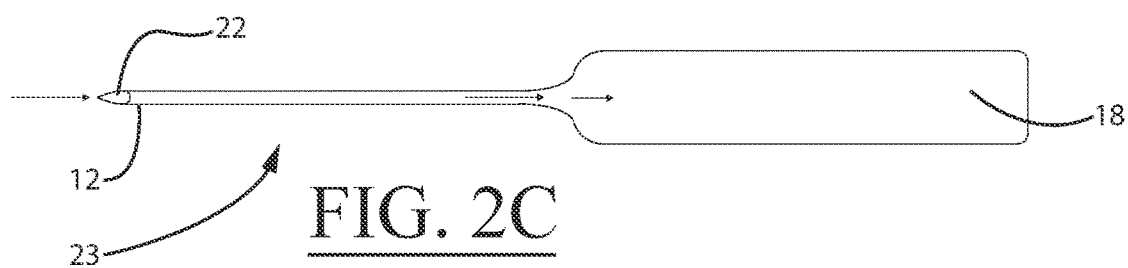
FIG. 2C is a side cross-sectional view of the needle and bulb of the plungerless aspiration and/or injection device of FIG. 2A, wherein the housing has been removed from the device to better illustrate the needle and bulb.
Figure 2D:
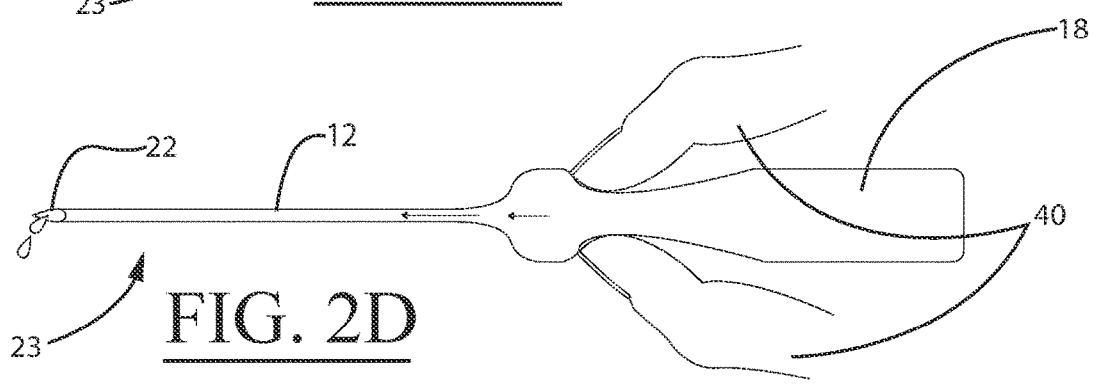
FIG. 2D is another side cross-sectional view of the needle and bulb of the plungerless aspiration and/or injection device of FIG. 2A, wherein the bulb is shown being compressed for active injection.
Figure 2E:
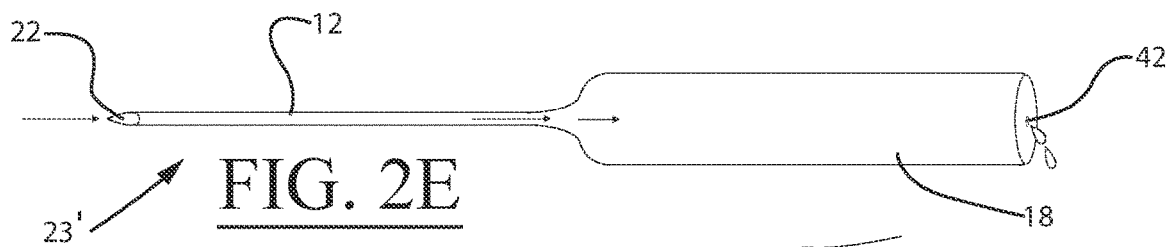
FIG. 2E is a side cross-sectional view of an alternative needle and bulb of the plungerless aspiration and/or injection device of FIG. 2A, where the bulb is provided with a drainage hole therein, and the bulb is shown being used for passive aspiration or drainage.
Figure 2F:
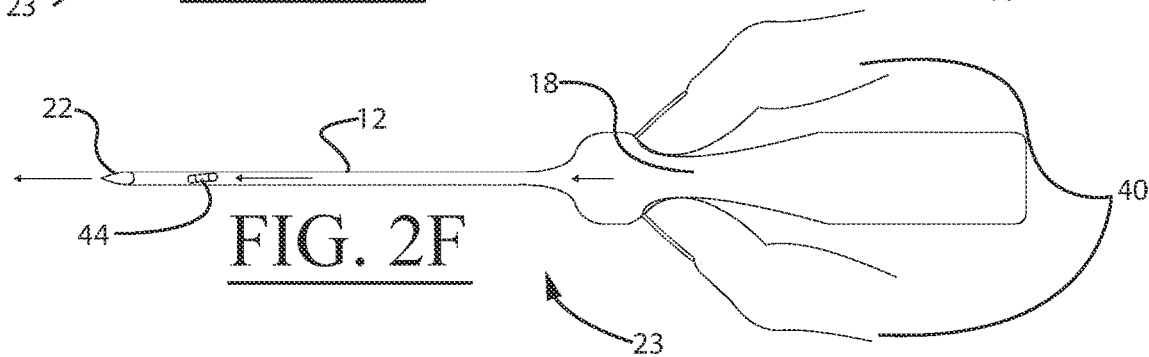
FIG. 2F is still another side cross-sectional view of the needle and bulb of the plungerless aspiration and/or injection device of FIG. 2A, wherein the bulb is shown being compressed for implantation of an implant.
Figure 2G:
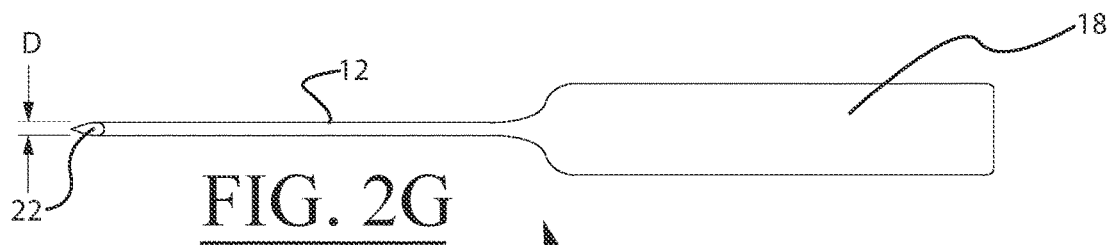
FIG. 2G is yet another side cross-sectional view of the needle and bulb of the plungerless aspiration and/or injection device of FIG. 2A.
Figure 2H:
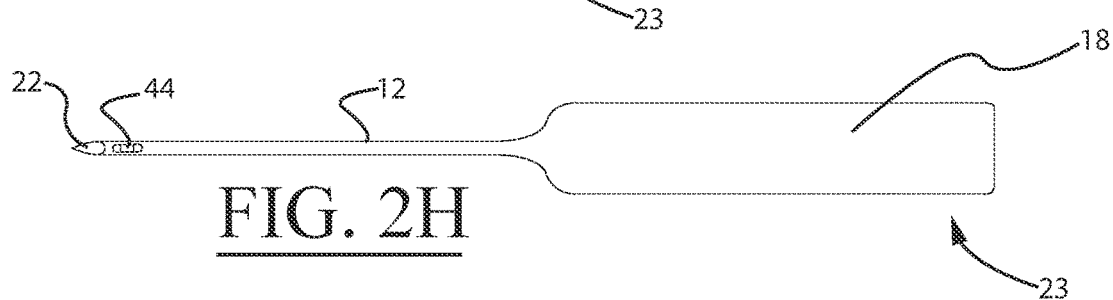
FIG. 2H is still another side cross-sectional view of the needle and bulb of the plungerless aspiration and/or injection device of FIG. 2A, wherein an implant is illustrated in the needle of the device.

The internal portion 23 of the illustrative plungerless aspiration and/or injection device 10 without the housing 16 is depicted in FIG. 2C. As shown in this figure, the internal portion 23 of the illustrative device 10 includes the needle portion 12 and the bulb portion 18. FIG. 2G depicts a view of the internal portion 23 of the illustrative device 10 similar to FIG. 2C, except that the needle diameter D of the needle portion 12 is labeled. In FIG. 2D, the bulb portion 18 of the internal portion 23 of the illustrative device 10 is shown being compressed by fingers 40 of a user during injection of a fluid. In FIG. 2E, an alternative embodiment of the internal portion 23' of the illustrative device 10, which has a drainage hole 42 disposed in the bulb portion 18, is shown being used for passive aspiration or drainage. In FIG. 2F, the bulb portion 18 of the internal portion 23 of the illustrative device 10 is shown being compressed by fingers 40 of a user during the implantation of an implant 44. FIG. 2H depicts a view of the internal portion 23 similar to FIG. 2F, except that the implant 44 is illustrated in the needle portion 12 prior to being injected when the bulb portion 18 is undeformed.

Figure 1D:
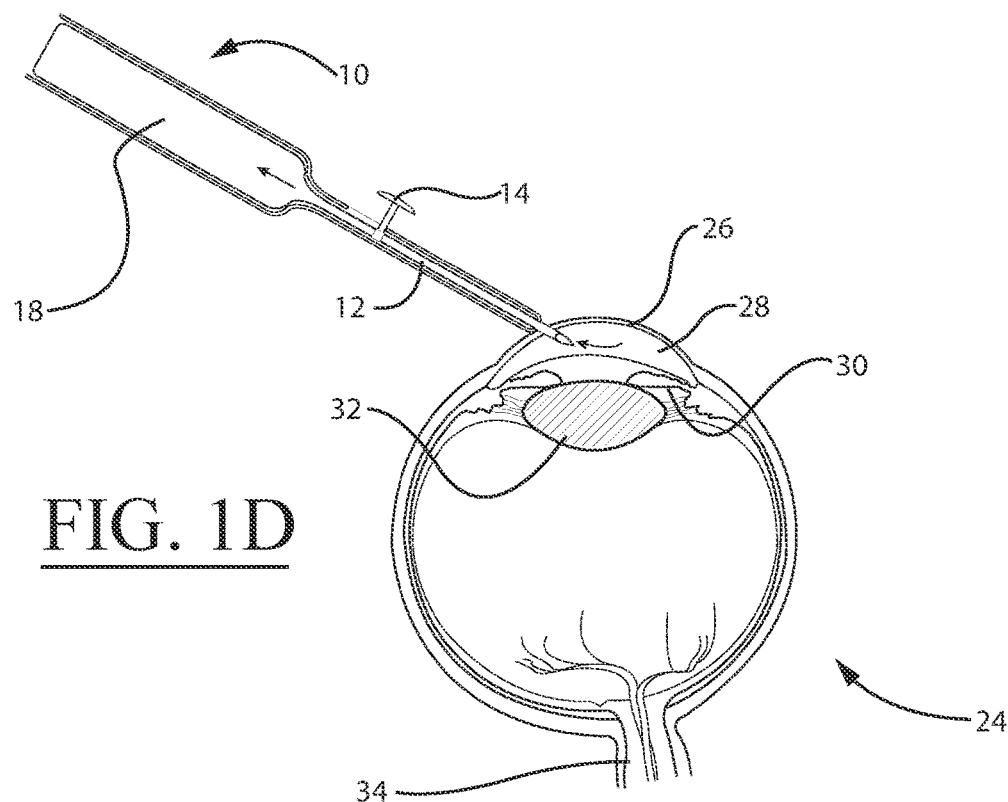
FIG. 1D is a side cross-sectional view of an eye, according to an illustrative embodiment of the invention, wherein the plungerless aspiration and/or injection device of FIG. 1A is being used to aspirate aqueous fluid from the anterior chamber of the eye.
Figure 1E:
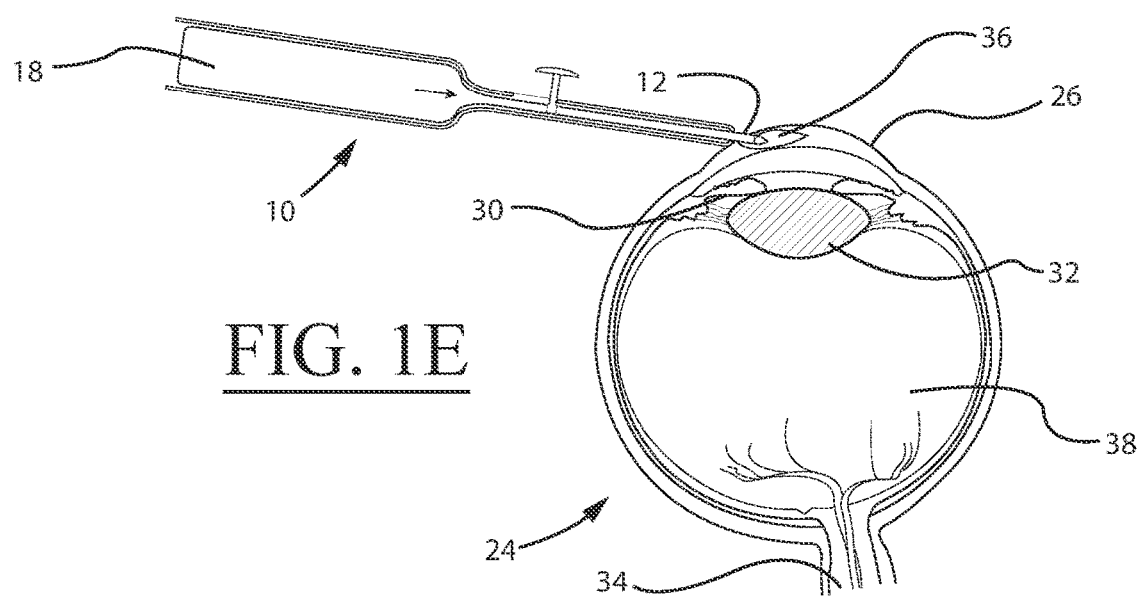
FIG. 1E is a side cross-sectional view of an eye, according to an illustrative embodiment of the invention, wherein the plungerless aspiration and/or injection device of FIG. 1A is being used for intracorneal cavity injection.

In FIG. 1D, an exemplary manner in which an aqueous fluid may be aspirated from the anterior chamber 28 behind the cornea 26 of an eye 24 using the device 10 is illustrated. The eye 24, as illustrated in FIG. 1D, further includes an iris 30, a lens 32, and an optic nerve 34. In FIG. 1E, an exemplary manner in which a substance may be injected into an intracorneal cavity 36 of an eye 24 using the device 10 is illustrated. The eye 24, as illustrated in FIG. 1E, further includes an iris 30, a lens 32, an optic nerve 34, and a vitreous cavity 38.

Figure 3A:
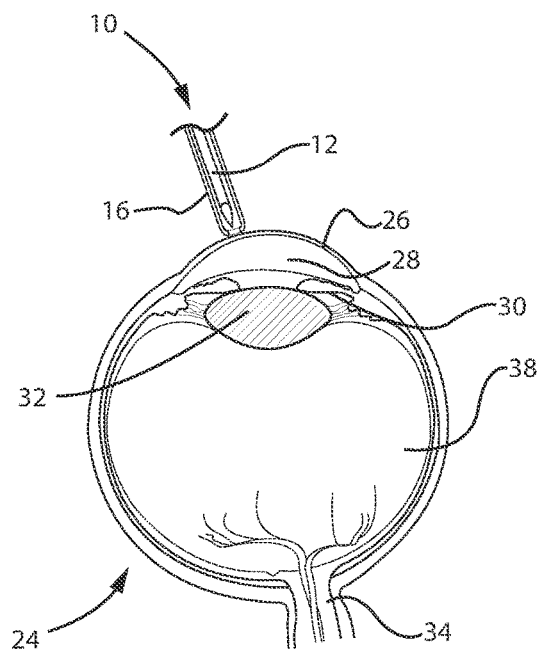
FIG. 3A is a side cross-sectional view of an eye, according to an illustrative embodiment of the invention, wherein the needle tip of the plungerless aspiration and/or injection device has not yet penetrated the cornea of the eye.
Figure 3B:
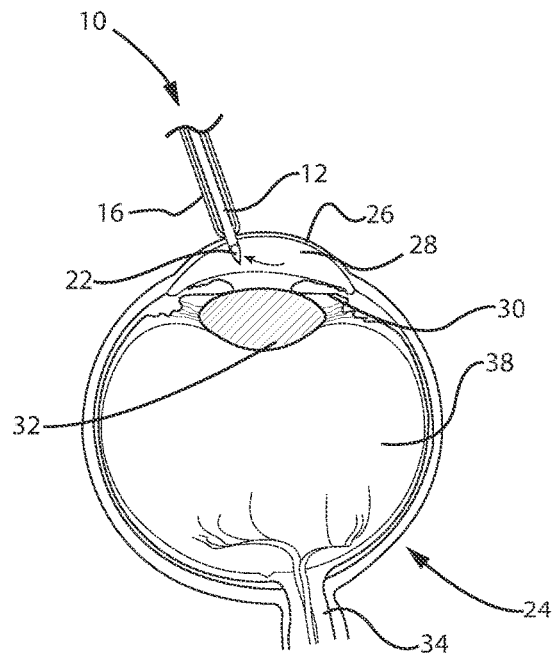
FIG. 3B is another side cross-sectional view of the eye of FIG. 3A, wherein the needle tip of the plungerless aspiration and/or injection device has penetrated the cornea of the eye so that aqueous fluid is able to be aspirated from the anterior chamber of the eye.

In FIGS. 3A and 3B, another exemplary manner in which an aqueous fluid may be aspirated from the anterior chamber 28 behind the cornea 26 of an eye 24 is illustrated. More specifically, FIG. 3A depicts the tip of the plungerless aspiration and/or injection device 10 proximate to the surface of the cornea 26 while the needle portion 12 of the device 10 is still retracted in the housing 16 of the device 10. FIG. 3B depicts the needle portion 12 of the device 10 inserted into the cornea 26, and aqueous fluid being aspirated from the anterior chamber 28 of the eye 24. The eye 24, as illustrated in FIGS. 3A and 3B, further includes an iris 30, a lens 32, an optic nerve 34, and a vitreous cavity 38.

Figure 3C:
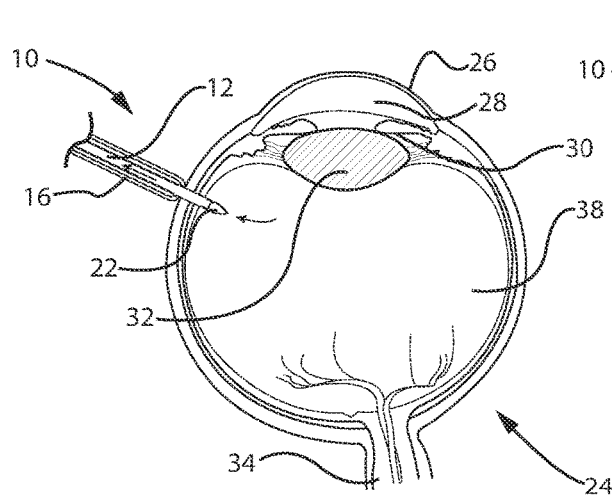
FIG. 3C is yet another side cross-sectional view of an eye, wherein the needle tip of the plungerless aspiration and/or injection device has penetrated the side of the eye so that vitreous fluid is able to be aspirated from the vitreous cavity of the eye.
Figure 3D:
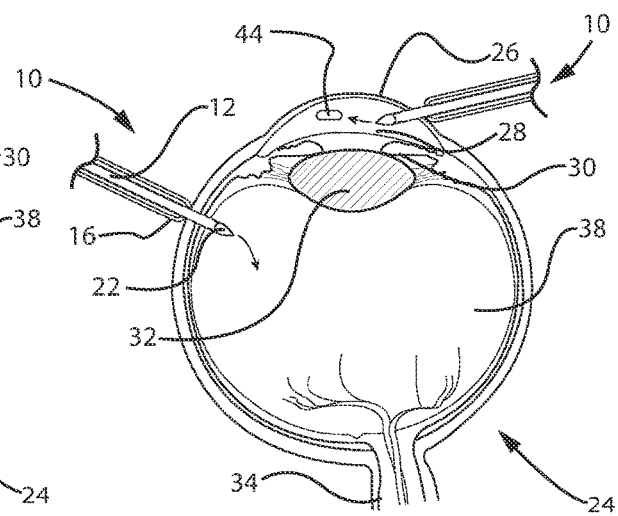
FIG. 3D is still another side cross-sectional view of an eye, wherein the plungerless aspiration and/or injection device is shown being used for injection or implantation in the anterior chamber of the eye, and the device is additionally shown being used for injection or implantation in the vitreous cavity of the eye.

In FIG. 3C, an exemplary manner in which vitreous humour may be aspirated from the vitreous cavity 38 of an eye 24 using the device 10 is illustrated. In FIG. 3D, an exemplary manner in which a fluid or implant may be injected into the vitreous cavity 38 of an eye 24 using the device 10 is illustrated. Also, in FIG. 3D, another device 10 is shown being used to inject a fluid or implant 44 in the anterior chamber 28 of the eye 24. The eye 24, as illustrated in FIGS. 3C and 3D, further includes a cornea 26, an iris 30, a lens 32, an optic nerve 34, and a vitreous cavity 38.

Figure 3E:
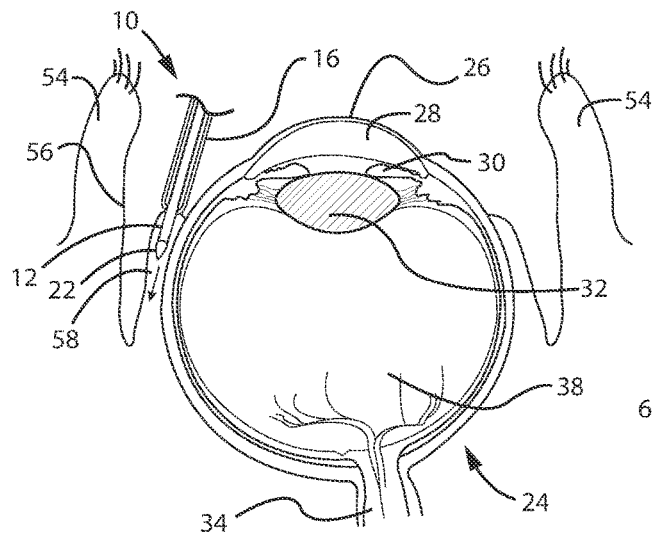
FIG. 3E is yet another side cross-sectional view of an eye, wherein the plungerless aspiration and/or injection device is shown being used for injection or implantation in the sub-conjunctival space of the eye.

In FIG. 3E, an exemplary manner in which a fluidic substance or implant may be injected into the subconjunctival space 58 of an eye 24 using the device 10 is illustrated. The eye 24, as illustrated in FIG. 3E, includes a cornea 26, an anterior chamber 28, iris 30, a lens 32, an optic nerve 34, a vitreous cavity 38, lids 54, and conjunctiva 56.

Figure 3F:
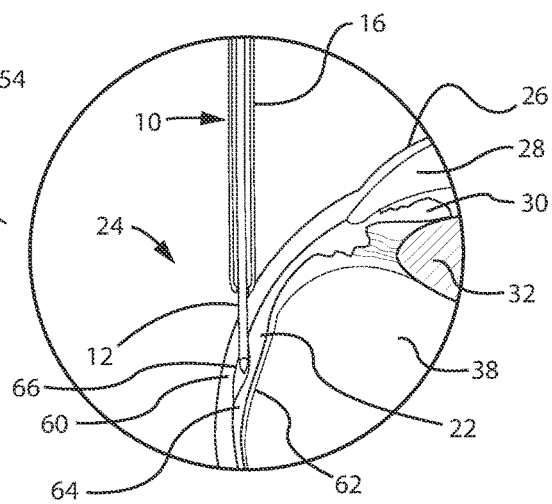
FIG. 3F is still another side cross-sectional view of an eye, wherein the plungerless aspiration and/or injection device is shown being used for injection or implantation in the suprachoroidal space of the eye.

In FIG. 3F, an exemplary manner in which a fluidic substance or implant may be injected into the suprachoroidal space 66 of an eye 24 using the device 10 is illustrated. The device 10 could also be used in a similar manner for aspiration from the suprachoroidal space 66. The eye 24, as illustrated in FIG. 3F, includes a cornea 26, an anterior chamber 28, iris 30, a lens 32, a vitreous cavity 38, a sclera 60, retina 62, and choroid 64.

Figure 3G:
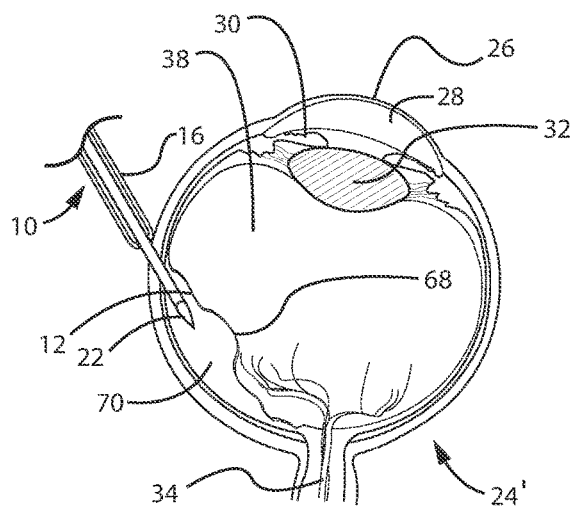
FIG. 3G is yet another side cross-sectional view of an eye, wherein the plungerless aspiration and/or injection device is shown being used for injection or implantation in the subretinal space of the eye.

In FIG. 3G, the eye 24' with cornea 26, anterior chamber 28, iris 30, a lens 32, optic nerve 34, and vitreous cavity 38 has a detached retina 68 that produces a subretinal space 70. The plungerless aspiration and/or injection device 10 may be used to aspirate a fluid from the subretinal space 70 during a medical procedure performed to reattach the retina 68.

Figure 3H:
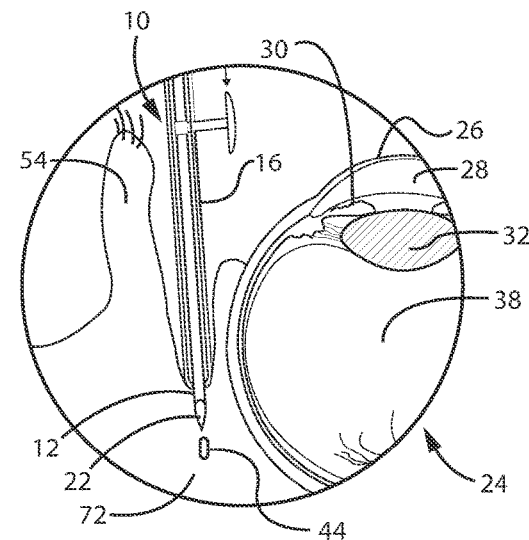
FIG. 3H is yet another side cross-sectional view of an eye, wherein the plungerless aspiration and/or injection device is shown being used for injection or implantation in the retrobulbar space of the eye.

In FIG. 3H, an exemplary manner in which a fluidic substance or implant 44 may be injected into the retrobulbar space 72 of an eye 24 using the device 10 is illustrated. The eye 24, as illustrated in FIG. 3H, includes a cornea 26, anterior chamber 28, iris 30, a lens 32, a vitreous cavity 38, and lid 54.

In one embodiment, the injection is done by actively pressing gently over the flexible spatula and the bulb inside it (refer to FIGS. 2A-2H).

In one embodiment, the needle is pushed in the tissue with the index finger moving the knob located in a slot in the external housing and while the needle is inside the cavity, by releasing slowly the bulb's semi-elastic body expanding automatically and aspirating gradually a small volume of the liquid from the fluid containing cavity, so that it can subsequently be analyzed outside the body using known diagnostic tools such spectrometer, microscope, staining for recognition of various bacteria, fungi, parasites, or viruses, or mass-spectroscopy, PCR, Raman spectroscopy or surface-enhanced Raman spectroscopy technique, enzyme-linked immunosorbent assay (ELISA) test strips, dot blots, solutions on slides, etc. In one embodiment, the biological fluid is anterior chamber fluid and the detection reagent detects a cytokine, etc.

In one embodiment, under normal conditions, the needle tip is retracted and inside the outer metallic, plastic, or glass tube housing, etc. This permits positioning of the instrument with its dull tip end of outer housing to be moved over the tissue surface or inside the tissue and to select a desired location without scratching or cutting the sensitive tissue surface, such as the cornea, skin, mucosa, or choroid, etc.

In one embodiment, the injector carries functionalized antibody-coated nanoparticles with pluralities of nanoparticles conjugated with checkpoint inhibitors and oncolytic viruses to be injected inside a tumor to release the medication as a response to external energy, such as laser, alternating magnetic field, or a focused ultrasound, to treat an external or internal tumor, such as melanomas or precancerous melanoma inside the eye or conjunctiva, lid tumors, breast cancer, prostate cancer, skin tumors, such as squamous cancer or basal cell cancer of the skin.

In one embodiment, the needle can be moved forward or backward by moving a knob connected to the inner needle forward or backward, since the silicone bulb is connected to the needle's end, but is elastic and not fixed to its housing, it can also travel inside the housing forward or backward by the same exposed knob (see FIGS. 1A-1E and FIGS. 2A-2B).

In one embodiment, the needle can be any size with the lengths of 1 mm to 100 mm or more.

In one embodiment, the needle has a diameter of 0.001 mm to 1 mm or more.

In one embodiment, the bulb reservoir by its connection to outside is filled with the air, gas, etc.

In one embodiment, the bulb is filled with a liquid solution or emulsion.

In one embodiment, the bulb is filled with an emulsion containing nanoparticles, microparticles, or larger particles.

In one embodiment, the bulb reservoir contains a viscoelastic material.

In another embodiment, the viscoelastic contains medication or a photosensitizer, such as riboflavin or Porphyrin derivatives, methylene blue or indium, platinum, rhodium plus albumin, eosin, rose Bengal, phthalocyanines, carotenoids, semiconductor nanoparticles, etc. that is activated under ultraviolet (UV) or another radiation to crosslink proteins of an organism.

In one embodiment, the injector is filled with a photosensitizer and an antibiotic, an antifungal, an antiviral, an anticancer medication, anti-parasites, etc.

In one embodiment, the injector is filled with functionalized thermosensitive nanoparticles, such as gold, iron oxide, carbon nanotubes, or thermosensitive polymers, such as liposomes, solid lipids, micelles, nanobubbles, etc. to carry medications in the form of slow release compounds and release the medication after administration.

In one embodiment, the injector carries functionalized antibody-coated nanoparticles with pluralities of nanoparticles conjugated with checkpoint inhibitors and oncolytic viruses to be injected inside a tumor to release the medication as a response to external energy, such as a laser, alternating magnetic field, or a focused ultrasound, to treat an external or internal tumor, such as melanomas or pre-cancerous melanoma, inside the eye or conjunctival or lid tumors, breast cancer, prostate cancer, skin tumors such as squamous cancer or basal cell cancer of the skin.

In one embodiment, the fluid is a viscoelastic material and contains a medication in form of an emulsion containing nanoparticles or micro-particles having a diameter of 1-1000 nm.

In one embodiment, the fluid is a viscoelastic material (e.g., hyaluronic acid or 0.01-1% or more).

In one embodiment, the viscoelastic material is made from another compound.

In another embodiment, the viscoelastic material contains a medication in the form of polymeric slow release nanoparticles or micro-particles of 1-1000 microns or more.

In one embodiment, the polymeric slow release nanoparticles or micro-particles or the implant injected to release medication is made from liposomes, micelles, nano- and micro-particulates of polylactic, polycyclic acid, or in combination with PGLA or porous silicone, nanoparticles of hydrogel, or polyesters, such as polycaprolactone, or other compounds such as chitosan, solid lipids, collagen, alginate dendrimers, metallic nanoparticles such as gold tubes filled with polymeric medications, etc.

In one embodiment, the nanoparticles can be functionalized to attach to certain cells, organisms, bacteria, etc.

In one embodiment, the viscoelastic material carries with it an implant with a diameter of 0.02-2 mm or more.

In one embodiment, the implant can have a length of 0.01-5 mm or more.

In one embodiment, the inner tube is filled with a polymeric drug delivery implant with a diameter of 20-1000 microns and a length of 0.02-100 mm or more as needed.

In one embodiment, the drug or fluid administration, etc. does not require an incision to be made in the tissue (e.g., with a knife, etc.), but the drug or the fluid is administered with the needle's sharp end, which does not require an incision for injection or a suture for its closure.

In one embodiment, the injection is done preferably in an angulated direction to the surface of the tissue that permits the tissue around the injection to close like a valve by the tissue pressure or increased pressure inside the tissue or the cavity after the injection preventing expulsion of the medication or the implant.

In one embodiment, the housing of the needle is positioned over the desired area, then the sharp needle's tip is slowly or gradually moved forward inside the tissue under observation to see the needle tip (e.g., inside the corneal pocket or inside the anterior chamber, etc.) by moving the instrument's knob forward to the desired distance and a desired direction in the tissue of the cavity, then compressing the medication-filled elastic bulb reservoir to release the medication under the observation of the needle's tip in the desired place (refer to FIGS. 2A-2I and FIGS. 3A-3H).

In one embodiment, the housing of the needle is positioned over the desired area, then the sharp needle tip is slowly or gradually moved forward inside the tissue under observation to see the needle tip by moving the instrument's knob forward to the desired distance and desired direction in the tissue or inside the cavity, then compressing the elastic bulb through the elastic forked housing over the bulb. The elastic thin-walled fork over the bulb provides a more controllable pressure to the bulb filled with the medication, etc. to be compressed between the thumb and index finger to slowly release the medication in the desired area or stop at a desired time (see FIGS. 2A, 2B, 2D, and 2F).

In one embodiment, the housing of the needle is positioned over the desired area, then the sharp needle tip is moved slowly or gradually forward inside the tissue under observation to see the needle tip by moving the instrument the knob forward to a desired distance and desired direction in the tissue of the cavity while the bulb is compressed, then the compression of the bulb is released slowly to aspirate fluidic biopsy to a desired volume, the biopsy fluid for subsequent analysis as described (refer to FIGS. 2C and 2E).

In one embodiment, the sharp tip of the needle is used inside the tissue, e.g., inside the cornea after femtosecond laser application or a Small Incision Lenticule Extraction (SMILE) procedure to dissect the bridges of the tissue with ease.

In one embodiment, the instrument is equipped with a graded flexible guard that indicates how much fluid or medication is injected in a cavity (e.g., vitreous cavity, in the anterior chamber, under the conjunctival, inside the vitreous cavity, in the suprachoroidal space, under the retina, or anywhere else—see FIG. 2I and FIGS. 3A-3H).

Figure 2I:
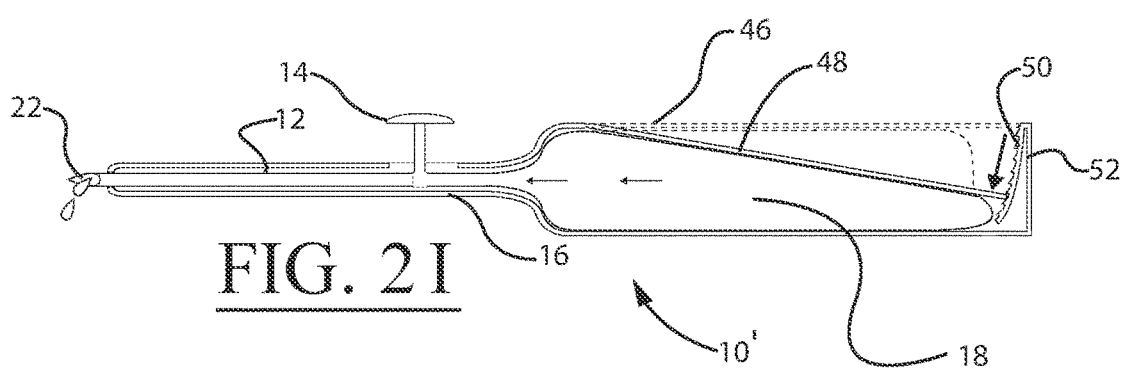
FIG. 2I is a side cross-sectional view of a plungerless aspiration and/or injection device, according to yet another illustrative embodiment of the invention, wherein the bulb of the device is incrementally compressed using a flexible angulated step ladder-like structure.

In one alternative embodiment, as shown in FIG. 2I, by pressing the flexible guard 46 over the bulb 18, a fluid is injected using the plungerless aspiration and/or injection device 10'. In this alternative embodiment, the housing 16 is also equipped with a flexible step ladder stopper 50 either as a rectangular plate or a ring-shaped plate with deep grooves, by pressing one of the forked blades 48 of the housing 16, it falls inside first groove indicating, e.g., 0.05 ml of the fluid is expelled out while making a clicking sound. In one embodiment, one can build the stopper so that each step (groove) would indicate how much more fluid volume is injected inside a cavity from 0.05 to 0.5 ml to 0.1 ml-2.05 ml, etc. as needed precisely (refer to FIG. 2I).

As shown in the alternative embodiment of FIG. 2I, to inject a predetermined amount of a fluid, a user presses the flexible guard 46 over the bulb 18 until the proximal end of the forked blade or pivotable lever 48 seats within one of the grooves in the angulated stepped internal wall 50 of the plungerless aspiration and/or injection device 10', wherein the groove corresponds to a predetermined amount of fluid being discharged from the device 10'. In FIG. 2I, it can be seen that the proximal end of the device 10' is closed by an end cap 52, which is attached to the angulated stepped internal wall 50.

In one embodiment, the needle is inserted inside the tissue or a cavity and the medication, fluid, gas or implant is expelled out by simply applying pressure to the bulb.

In one embodiment, the instrument can be used as a passive system for collection of fluid biopsy from the blood or a body cavity by creating a small hole in the wall of the bulb to release fluid from the body cavity through the needle to the silicone bulb to outside where it can be collected as desired (refer to FIG. 2E).

In one embodiment, a silicone tube is connected to the needle and the external end is connected to an elastic silicone tube to drain the fluid out of the eye cavity in a passive way that can be clamped at any time as known in the art.

In one embodiment, the device permits removal of a small amount of fluid of 0.1 microliters to milliliter, etc. as needed for the analysis either in bacterial, fungal, viruses, parasites, etc. infection, or malaria detection, circulating tumor cells, exosomes, micro-RNS, micro-DNA, antibodies indicating one or other disease process in the eye fluid or elsewhere in a body cavity.

In one embodiment, the needle is inserted in the suprachoroidal space while a thin flexible metallic wire is pushed through it to drain fluid of a pigment epithelial detachment, by inserting the wire from the back into a pigment epithelial detachment space and draining passively the fluid in the choroidal space in the pigment epithelial detachment (see FIG. 3F).

In one embodiment, the silicone bulb can be injected with the medication in liquid or emulsion form or an implant form that can pass through the wall diameter of the needle prior to release of the medication or implant in the eye cavity, corneal cavity, subconjunctival space in the lens capsule after cataract extraction in the lens capsule, or in the sub-retinal space or in the choroid.

In one embodiment, the instrument's needle can be inserted in any place in the eye (refer to FIGS. 3A-3H) or outside the eye (e.g., in the joints, mouth, bladder, vagina, nose, ear, etc., cerebrospinal fluid, etc. to take either a fluid biopsy or injected medication).

In one embodiment, the flexible bulb is used to drop the medication as a drop, or spray the liquid medication of emulsion over or inside a body cavity or over the cornea or under the lid or over the conjunctiva, or over a body's mucosa by compressing rapidly the flexible tail of the instrument with the bulb reservoir to spread the medication in the cavity.

In one embodiment, the medications that are administered using this instrument are steroids, anti-inflammatory agents, NSAIDs, Rock inhibitors, integrin inhibitors, GSK inhibitors alone or in combination in slow release nanoparticle polymers, such as polylactic or glycolic acid, micelles, liposomes, porous silicon, or polyester, and is administered precisely to release the medication in the cornea or inside a body tissue or cavity for a long time after implantation.

In one embodiment, the medications that are administered using this instrument are anti-inflammatory agents, such as Rock inhibitors, GSK inhibitors, integrin inhibitors, alone or in combination with immunosuppressants such as cyclosporine, Mycophenolic acid, ascomycin, metalloproteinase inhibitors, such as doxycycline, tetracycline, etc. or low molecular weight heparin, alone or in combination in slow release nanoparticle or microparticle polymers, such as polylactic or glycolic acid, micelles, liposomes, porous silicon, or polyester to release the medication in the cornea or inside a body tissue or cavity for a long time after implantation.

In one embodiment, the unit can be prefilled with specific non-toxic doses of antibiotics, antivirals, anti-parasites, antifungals, or antivirals, etc. in a solution or emulsion of nanoparticles for slow release of the medication.

In one embodiment, the disease process involves the cornea, glaucoma, dry eye, uveitis, retinal detachment, refractive surgery and corneal implantation, optic nerve inflammation, retinitis pigmentosa, diabetic retinopathy, age-related macular degeneration wet or dry form, glaucoma, scleritis and the medication is injected in the cavity or inside the tissue as shown in FIG. 3.

In one embodiment, the instrument can be made sterile with pre-filled medication as a disposable unit to deliver the medication to the quantity/volume as needed.

In one embodiment, the unit can have one or multiple medications, packaged sterile with pre-filled medications as a disposable unit for single use on a patient.

In another embodiment, the unit is sterilized and packaged, and is used for aspiration of a liquid biopsy as a disposable unit for single use on a patient.

In one embodiment, the plungerless injector and aspirator is used for vaccination.

In one embodiment, vaccination induces an immune response to an antigen where the antigen can be attenuated or dead viruses, attenuated or dead bacteria, attenuated or dead fungi, attenuated or dead parasites, or attenuated or dead tumor cells.

In one embodiment, the instrument is used for a single injection, and then disposed of without being used again.

In one embodiment, the vaccine can be administered intramuscularly, subcutaneously, intravenously, intra-arterially, or inside a body's cavity as a drop or spray in a liquid or aerosolized form through the nose, mouth, vagina, bladder, skin or injected in a tumor, inside a lesion or can be taken orally sublingually as emulsion of nanoparticles or microparticles, or through the intestinal tract, etc.

In one embodiment, the needle part of the injector can have a diameter of 10 microns to 2 mm or more with a length of 0.1 mm to 50 mm or more.

In one embodiment, the needle is covered with anticoagulant so that the blood does not coagulate inside the needle for venous micro-puncture or micro-aspiration to obtain a small amount of fluid for diagnostic purposes.

In one embodiment, the antiviral vaccine is made from dead viruses, or a part of the virus such as a lipid, protein, or polysaccharide, etc., or a part of the fungi, bacteria, parasites, or tumor cells, or it is made from mRNA or DNA or a part of them, or neutralized or crosslinked RNA or DNA of the viruses, bacteria, fungi, parasites, or tumor cells.

In one embodiment, the antigenic material of the vaccine is combined with either one or two or more medications, such as antivirals, antibacterials, anti-parasites, or anti-tumor medications, or a combination thereof.

In one embodiment, the instrument's chamber is filled with a liquid, semisolid, air or a gel or a mixture of them that can be injected or can create a spray for internal or external tissue, intranasally, inside the mouth, or inside a body cavity, such as vagina, uterus, bladder, or rectum.

In one embodiment, the instrument is used to withdraw blood from a vein or artery using the smallest possible needle since the blood will flow as soon as the needle tip enters the vessels, with the wall of the needle being coated with heparin to prevent blood clot formation.

In one embodiment, the outer tube of the needle can be 0.1 mm in length to 2.0 cm or more in length, and the active part of the unit can be of the same length or larger depending on where it is inserted at a desired distance outside or inside the body cavity.

In one embodiment, the cavity can be created inside a tissue with the sharp edge of the needle so that the rest of the needle and its outer tube can be placed inside the cavity and its flexible balloon can be filled with a medication, a solid implant, a semisolid implant, or an emulsion of nanoparticles or microparticles or larger particles, such as solid or semisolid particles of a few millimeters, or can be injected along with a fluid or viscoelastic material to lubricate the way of the injection (e.g., one creates a subcutaneous cavity, intracorneal cavity, a sub-conjunctival cavity, sub-mucosal cavity). The instrument is pushed in the cavity or inside an existing cavity such as the nose, mouth, etc. to spray the nose, mouth, pharynx, or inside a body cavity, such as in the bladder, entering through the ureter, etc.

In one embodiment, the plungerless injector and/or aspirator is in a form of a catheter with a double tube, nasal aspiration, and drop or spray. In this embodiment, the nozzle of the plungerless injector and/or aspirator is made of a solid injectable needle and its outer tube is made out of a soft synthetic polymer with various lengths that can be used to carry medication(s) through the ureter into the bladder or to empty the bladder.

In one embodiment, the inner tube can carry anti-neoplastic medications along with cellular inflammatory pathway inhibitors, antibacterials, antivirals, antifungals, antitumoral medication, etc. that can be applied to the wall of the bladder or ureter for irrigation and aspiration, etc.

In one embodiment, the tip of the aspiration-injection needle is made from solid or semisolid matter so that the sharp tip of the needle penetrates the skin or mucosa, or the corneal tissue for 0 to 200 microns or more where the compressible section of the unit is filled with non-toxic dark nanoparticles or microparticles are injected inside the desired part of the central cornea creating a ring of 1-3 mm tattooed area leaving a central clear portion of 1-2 mm transparent area for the light to pass through it functioning as a pinhole to treat presbyopia, myopia, and reduce the astigmatic aberrations of the cornea.

In one embodiment, a central 2-3 mm diameter portion of a corneal inlay is tattooed to create a dark spot and after tattooing the central 1.6 mm circle is removed with a trephine to create a pinhole before or after its implantation as a corneal inlay.

In one embodiment, the plungerless injector and/or aspirator is used for the machine-assisted injection of the skin, mucosa for a desired superficial or a deeper layer of the skin or sub-cutaneous tissue where the needle deposits desired medication to a lesion, or the polymeric nanoparticles act as a slow release implant for 3-6 months or more.

In one embodiment for vaccination or injection inside the tissue, the conical or frustoconical-shaped head of the unit is pressed over the skin to numb the subcutaneous nerves prior to the injection, thus creating a painless administration of a vaccine or injection inside the knee joints or the shoulder area, spinal cord, or injection inside the finger joints or toe joints, where the medication may be included with or without a viscoelastic that can be injected for cosmetic reconstruction of the face using Botox, etc.

Figure 4:
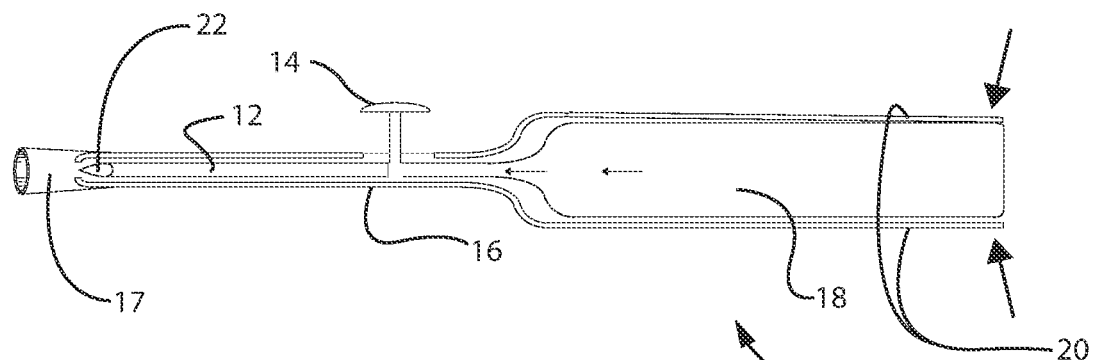
FIG. 4 is a side cross-sectional view of a plungerless aspiration and/or injection device, according to another illustrative embodiment of the invention, wherein the needle of the device is in a retracted position, and the housing is provided with an inverted frustoconical end portion.
Figure 5:
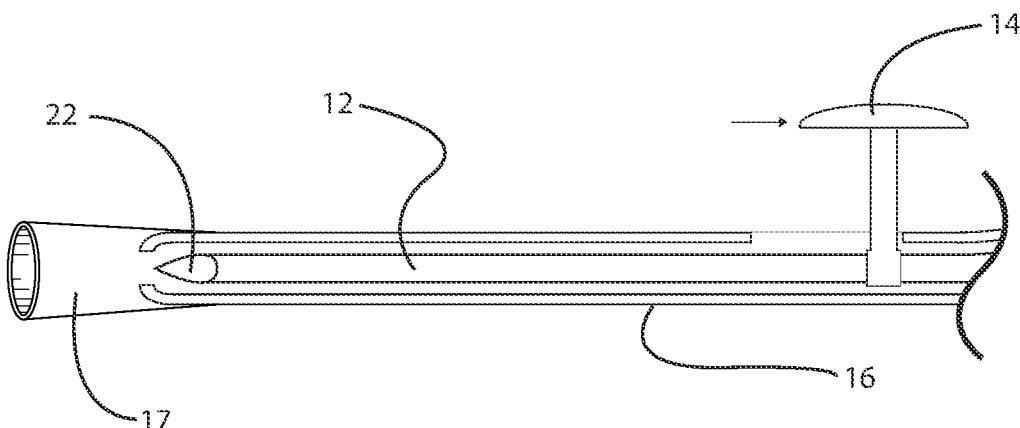
FIG. 5 is a partial side cross-sectional view of a distal end of the plungerless aspiration and/or injection device of FIG. 4, wherein the needle of the device is in a retracted position.
Figure 6:
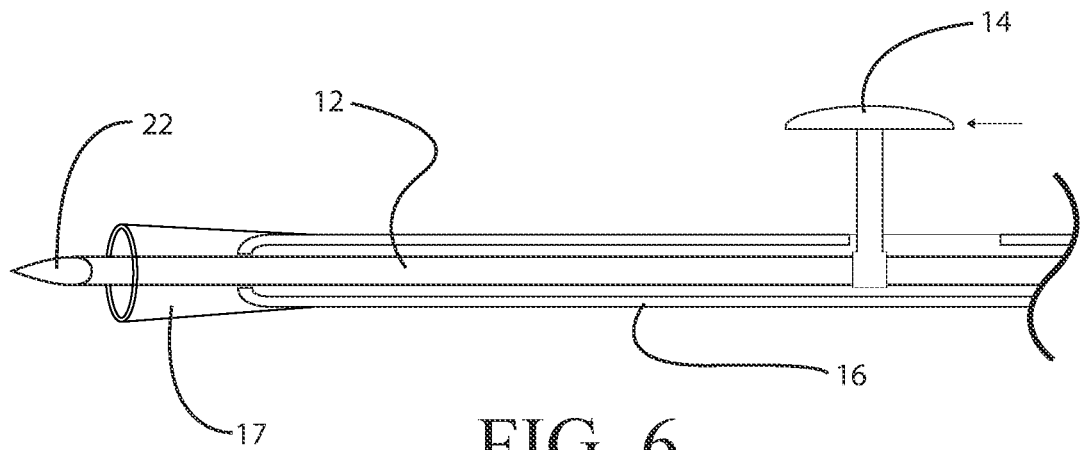
FIG. 6 is a partial side cross-sectional view of a distal end of the plungerless aspiration and/or injection device of FIG. 4, wherein the needle of the device is in an extended, exposed position.

Another illustrative embodiment of the plungerless aspiration and/or injection device is shown in FIGS. 4-6. The plungerless aspiration and/or injection device 10" depicted in FIGS. 4-6 includes a frustoconical-shaped head or end portion (i.e., an inverted frustoconical-shaped head or end portion). In the illustrative embodiment of FIGS. 4-6, the plungerless aspiration and/or injection device 10" comprises a housing 16, the housing 16 including an inverted frustoconical end portion 17 extending outwardly from the housing 16, the inverted frustoconical end portion 17 having an outer edge that is configured to be pressed against the skin of a patient; a needle portion 12 disposed in the housing 16, the needle portion 12 configured to be selectively retracted and extended by a user, the needle portion 12 comprising a needle tip 22 configured to be inserted into tissue of the patient for aspiration, injection, and/or implantation, and the needle tip 22 configured to be extended beyond the outer edge of the inverted frustoconical end portion 17 of the housing 16 (as shown in FIG. 6); and a bulb portion 18 disposed in the housing 16, the bulb portion 18 defining a fluid containing cavity that is fluidly coupled to the needle portion 12, and the bulb portion 18 being elastically deformable so that the user is able to perform the aspiration, the injection, and/or the implantation on the patient by manipulating the bulb portion 18. In the illustrative embodiment, the outer edge of the inverted frustoconical end portion 17 of the housing 16 is configured to be pressed against the skin of the patient prior to insertion of the needle tip 22 of the needle portion 12 into the skin of the patient so as to reduce a pain sensation of the patient resulting from the insertion of the needle tip 22 of the needle portion 12.

Referring again to FIGS. 4-6, it can be seen that, in the illustrative embodiment, the plungerless aspiration and/or injection device 10" further comprising a knob 14 for manipulating the needle portion 12, the knob 14 being slidably disposed within a slot of the housing 16. When the knob 14 is moved in a first direction by the user, the needle portion 12 is retracted into the housing 16. Conversely, when the knob 14 is moved in a second, opposite direction by the user, the needle portion 12 is extended out of the housing 16. In the illustrative embodiment, the bulb portion 18 is connected to the needle portion 12 such that the bulb portion 18 is displaced with the needle portion 12 when the knob 14 is moved in the first direction or second direction by the user.

In the illustrative embodiment, as best shown in FIG. 4, the housing 16 comprises elastically deformable forked blades 20 disposed over the bulb 18, the elastically deformable forked blades 20 configured to be depressed by the user between a thumb and index finger of the user so as to more controllably regulate a flow of fluid out of, or into the needle tip 22. The forked blades 20 may be spring-loaded to return to their undepressed state after being depressed by the user.

In one embodiment, the plungerless unit also can be used for administering medication in a slow release form to the scalp to bring nutrition or medication to the hair follicles, such as finasteride, etc. or Rock inhibitors for hair growth or along with hair transplantation to prevent inflammation or rejection of a transplant or to treat an infection, etc., or with the medication along with Rock inhibitors, Wnt inhibitors, GSK inhibitors, or integrin inhibitors to enhance cell proliferation or administering medications such as antibacterials, antivirals, anti-fungals, anti-neoplastic medications, etc.

In one embodiment, progenitor cells can be injected along with a Rock inhibitor, a Wnt inhibitor, or integrin inhibitors to encourage cell growth, such as corneal endothelial cell growth, or injected inside the retina or subretinal with nerve cell progenitors or mesenchymal stem cells, etc. to grow inside the tissue, e.g., in age-related macular degeneration, etc.

In one embodiment, the system can be placed inside the joints, inside a cutaneous lesion, or inside the anterior chamber of the eye, in the nose, mouth, etc. to take fluid samples, etc. for biopsy, chemical analysis, or to recognize an infection or a malignancy, etc.

In one embodiment, the unit is used to spray or nebulize medications, or a vaccine, etc., and can be administered intranasally or for inhalation through the nose or mouth or spraying medication on the surface of the skin or mucosa such as the mouth, nose, vagina, or anal application of various medications to assist in treating patient with severe constipation or deliver microbiomes, or to treat an infection, such as viral, bacterial, etc. so that the medication is absorbed through the nasal mucosa via the olfactory nerves or the 5th nerve trigeminus, transporting medication to the brain to treat a brain infection or treat a patient with severe depression (e.g., applying ketamine) or Rock inhibitors for a patient with traumatic brain injury, Alzheimer's disease or Parkinson's disease, or administered to the eye for treatment of glaucoma with the medication as a nasal spray, conjunctival spray, subconjunctival injection of polymeric slow release nanoparticles or microparticles alone or Rock inhibitors with mycophenolic acid or low molecular heparin as micelles or liposomes to prevent redness of the conjunctiva after topical administration of Rock inhibitors.

In one embodiment, the unit delivers encapsulated medications, such as medications in micelles or liposomes that can break after a period of time to release appropriate medications.

In one embodiment, a vaccine administered superficially or subcutaneously by injection followed with or without application of focused ultrasound to enhance the spread of the vaccine or as a therapeutic vaccine with anti-neoplastic medications and Rock inhibitors as an adjuvant, antibacterial, antifungal, or antineoplastic medication with or without a monoclonal antibody or adjuvants, etc. to enhance the immune response in the body and locally kill the neoplasms, bacteria, viruses, fungi, or parasites.

In one embodiment, the unit is made disposable for a single use with a predetermined amount of medication to inject medications in a liquid, semi-liquid, gel, or as polymeric slow release nanoparticles or microparticles, etc. for slow release from the polymeric nanoparticles or microparticles injected at any desired place in the body.

In one embodiment, the flexible balloon is filled with a viscoelastic material and a semi-solid polymeric compound, such as a flexible intraocular lens that can pressed through the nozzle of the unit to be injected, e.g., after removal of a cataract inside the lens capsule just by compressing the balloon with two fingers or a glaucoma shunt can be injected in the Schlemm's canal through the trabecular meshwork of the eye.

In one embodiment, an intracorneal inlay is placed inside the balloon of the plungerless injector and/or aspirator unit filled with a viscoelastic fluid, where the corneal inlay is to be placed inside a corneal cavity prepared with a femtosecond laser and the conical or frustoconical-shaped tip of the unit cannot only penetrate the cornea, but also, if needed, create a cavity with its sharp needle and eject the corneal inlay into the corneal cavity to modify refractive error of the eye or enhance the mechanical properties of a soft cornea, such as in keratoconus.

In one embodiment, the unit is used for intracorneal injection or subconjunctival injection, suprachoroidal injection, or subretinal or intraocular injection, or in the lens capsule after cataract surgery delivering various medications, e.g., such as micelles, liposomes, gel, or as slow release polymeric nanoparticles or microparticles carrying the medications.

In one embodiment, piezoelectric nanoparticles or microparticles are injected with the use of the injector in the vitreous cavity to migrate in the retina, or injected under the retina to migrate under the retina gradually, or in the retina through the intercellular spaces of the retinal cells to stimulate the retinal cells when stimulated with the ultrasound from outside the eye.

In one embodiment, because the nanoparticles or microparticles have a small size, the particles can mold to the back side of the retina and the retinal pigment epithelium, while permitting nutrition and fluid to pass around the nanoparticles or microparticles to reach the entire thickness of the retina in contrast to the previously implanted plate of electrodes, etc. that would block nutrition of the retina (see e.g., Peyman et al., "Subretinal semiconductor microphotodiode array", Ophthalmic Surgery and Lasers; Thorofare Vol. 29, Iss. 3, (March 1998): pp. 234-241, the disclosure of which is hereby incorporated by reference as if set forth in its entirety herein).

In one embodiment using an injector and aspirator carrying the nanoparticles or piezoelectric nanoparticles, a gene-CRISPR/cas9 complex can be administered through the vitreous cavity or preferably in the superior subretinal space so that with time the nanoparticles and microparticles migrate toward the sub-foveal space under the retina or through the intracellular spaces to reach the central retina and can be stimulated with ultrasound or light to enhance gene delivery after light or ultrasound stimulation, inducing an electrical cell membrane polarization or depolarization which opens the cell membrane pores permitting the genes to enter the cells cytoplasm in the macular area of the retina and target the mutated DNA, cut to remove it, or replace it with an unmutated DNA segment.

In one embodiment, the unit is used to deliver the medication as slow release polymers or gel in the vitreous cavity, subretinal space, retrobulbar injection, or for subcutaneous slow release of medications, or for nasal single dose inhalation, spray or nebulization for treatment of various diseases, such as allergies, bacteria, viruses, or fungi, etc., affecting the nose, eye, throat, bronchi, lung, or brain, etc.

In one embodiment, the piezoelectric nanoparticles or microparticles can be flexible piezoelectric microparticles, perovskite/wurtzite piezoelectric or Zno materials, or can be made biocompatible by encapsulating or coating them or using coupling agents such as phosphate, carbolate to modify the surface of the nanoparticles microparticles, or covering them with poly-L-Lysine, chitosan, etc. (e.g., refer to U.S. Pat. No. 10,022,457, entitled Methods to Regulate Polarization And Enhance Function of Cells, the disclosure of which is hereby incorporated by reference as if set forth in its entirety herein).

In one embodiment, the plungerless injector and/or aspirator is used either with a desired medication, e.g., an anti-VEGF or Rock inhibitor as topical drops on the corneal or conjunctiva or subconjunctival space, or along with slow release polymers in the vitreous, anterior chamber, or suprachoroidal space, or in the subretinal space to release medication slowly to penetrate retina for slow release of mediations or in conjunction with nerve progenitor stem cells or mesenchymal cells to migrate under the retina to the foveal area though the intercellular space or subretinal space gradually to prevent the foveal cell damage caused, e.g., by age-related macular degeneration dry or wet form, etc.

In one embodiment, the plungerless injector and/or aspirator is used either with a desired medication with neuronal progenitor cells, or along with slow release polymers in the suprachoroidal space, or in the subretinal space to release a medication, such as Rock inhibitors, Wnt inhibitors, GSK inhibitors, or integrin inhibitors to slowly penetrate the retina, or placed in the subretinal space for slow release of mediations, or in conjunction with progenitor nerve stem cells or mesenchymal cells to migrate under the retina to the central foveal area though the intercellular space and replace the retinal cell damage caused by age related macular degeneration or retinitis pigmentosa.

In one embodiment, the foveal drug or stem cell delivery to the center of the retina (fovea) is done without lifting the sensitive fovea by a novel injection in an area for 10-180 degrees of the superior retina through the sclera or through the vitreous cavity lifting only superior retina by the injection and leaving the sensitive fovea as "fovea sparing procedure" where the medications migrate by gravity through the retinal intercellular spaces to locate in the fovea without significantly lifting the fovea which would damage the fovea, e.g., in a patient with age-related macular degeneration or for gene delivery in various form of retinitis pigmentosa, or to cut and replace the mutated DNA or replace them with new gene using CRISPR-cas9, etc.

In one embodiment, the foveal drug or stem cell delivery or delivery of quantum dots, nanoparticles, or microparticles to the center of the retina (fovea) is done without lifting the sensitive fovea by a novel injection in an area for 10-180 degrees of the superior retina through the sclera or through the vitreous cavity lifting only the superior retina by the injection, while elevating the head and leaving the sensitive fovea as a "fovea sparing procedure" where the quantum dots migrate by gravity through the retinal intercellular spaces to locate in the fovea without significantly lifting the fovea, e.g., in patient with a genetic retinal disease, such as various forms of retinitis pigmentosa or Leber amaurosis congenital (LCA), etc., so that the disease process may be treated by gene delivery and CRISPR-Cas9, etc. to cut or replace the defective DNA or replace them.

In one embodiment, the foveal drug or stem cell delivery to the center of the retina (fovea) is done without lifting the sensitive fovea by a novel injection in an area for 10-180 degrees or more of the superior temporal retina through the sclera or through the vitreous cavity lifting only superior temporal retina by the injection and leaving the sensitive fovea as "fovea sparing procedure" where the medications migrate by gravity through the retinal intercellular spaces to locate in the fovea without significantly lifting the fovea which would damage the fovea, e.g., in a patient with genetic disease of the retina to inject piezoelectric nanoparticles or microparticles, that can be subsequently stimulated with ultrasound from outside to create an electric pulse in the retinal cells and initiate an action potential in the retinal cells that are in contact with the piezoelectric nanoparticles or microparticles to prevent their degeneration, since the retinal cells degenerate without an electric stimulation.

In one embodiment, the foveal drug or stem cell delivery to the center of the retina (fovea) is done along with administration of retinal stem cells or mesenchymal stem cells with a slow release polymeric nanoparticles carrying medication and one of Rock inhibitors, Wnt inhibitors, GSK inhibitors, or integrin inhibitors to prevent a postoperative inflammation for many months to years, or in combination with piezoelectric nanoparticles or microparticles where the injection is in the subretinal space through the sclera, or through the vitreous cavity under the subretinal space under microscopic observation, lifting only the desired retinal area by the injection and leaving the sensitive fovea untouched as a "fovea sparing procedure" where the medications migrate by gravity in the subretinal space or through the retinal intercellular spaces to locate in the fovea without significantly lifting the fovea which would damage the fovea, e.g., in a patient with genetic disease of the retina, etc.

In one embodiment, the quantum dot nanoparticles or piezoelectric nanoparticles and polymeric drug delivery nanoparticles for slow release medications are administered together or separately and injected only in the temporal or superior part of the retina to gradually penetrate the retina to reach the fovea through the intercellular spaces or subretinal spaces where the nanoparticles come into contact with the retinal ganglion cells and can be stimulated either with a non-toxic dose of a light source or ultrasound to generate electrical pulses to the retinal ganglion cells and other glial cells of the retina or the medications can be combined with gene therapy using CRISPR-cas9 with or without stem cell therapy to replace dead retinal cells or support retinal vasculature in diabetic retinopathy.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A plungerless aspiration and/or injection device, comprising:
   a housing, the housing including an end portion extending outwardly from the housing, the end portion having an outer edge that is configured to be pressed against a body portion of a patient;
   a needle portion disposed in the housing, the needle portion including a needle tip, and the needle tip configured to be extended beyond the outer edge of the end portion of the housing;
   a knob for manipulating the needle portion, the knob being slidably disposed within a slot of the housing; and
   a bulb portion disposed in the housing, the bulb portion defining a fluid containing cavity that is fluidly coupled to the needle portion, and the bulb portion being elastically deformable so that the user is able to perform aspiration, injection, and/or implantation on the patient by manipulating the bulb portion;
   wherein the outer edge of the end portion of the housing is configured to be pressed against the body portion of the patient prior to insertion of the needle tip of the needle portion into the body portion of the patient so as to reduce a pain sensation of the patient resulting from the insertion of the needle tip of the needle portion;
   wherein, when the knob is moved in a first direction by the user, the needle portion is retracted into the housing;
   wherein, when the knob is moved in a second direction by the user, the needle portion is extended out of the housing, the second direction being opposite to the first direction; and wherein the plungerless aspiration and/or injection device is configured such that a retraction and extension of the needle portion by the knob is independent from a manipulation of the bulb portion by the user.

2. The plungerless aspiration and/or injection device according to claim 1, wherein the end portion of the housing is an inverted conical end portion or inverted frustoconical end portion.

3. The plungerless aspiration and/or injection device according to claim 1, wherein the housing comprises elastically deformable forked blades disposed over the bulb, the elastically deformable forked blades configured to be depressed by the user between a thumb and index finger of the user so as to controllably regulate a flow of fluid out of, or into the needle tip.

4. The plungerless aspiration and/or injection device according to claim 3, wherein the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

5. The plungerless aspiration and/or injection device according to claim 1, wherein the needle portion has a 19 gauge to 44 gauge needle diameter.

6. The plungerless aspiration and/or injection device according to claim 1, wherein the needle portion has a diameter between approximately 0.001 millimeters and approximately 1.0 millimeters.

7. The plungerless aspiration and/or injection device according to claim 1, wherein the needle portion has a needle length between approximately 1 millimeter and approximately 100 millimeters.

8. The plungerless aspiration and/or injection device according to claim 1, wherein the bulb portion is formed from a compressible silicone, rubber, or other elastic polymer.

9. The plungerless aspiration and/or injection device according to claim 1, wherein the housing comprises a graded flexible guard that indicates the amount of the fluid or medication that is injected in a body cavity.

10. A method of using a plungerless aspiration and/or injection device, said method comprising the steps of:
providing a plungerless aspiration and/or injection device that includes:
a housing, the housing including an end portion extending outwardly from the housing, the end portion having an outer edge that is configured to be pressed against a body portion of a patient;
a needle portion disposed in the housing, the needle portion including a needle tip, and the needle tip configured to be extended beyond the outer edge of the end portion of the housing; and
a bulb portion disposed in the housing, the bulb portion defining a fluid containing cavity that is fluidly coupled to the needle portion, and the bulb portion being elastically deformable so that the user is able to perform aspiration, injection, and/or implantation on the patient by manipulating the bulb portion;
filling the fluid containing cavity of the bulb portion with non-toxic dark nanoparticles or microparticles;
pressing the outer edge of the end portion of the housing against the body portion of the patient prior to insertion of the needle tip of the needle portion into the body portion of the patient so as to reduce a pain sensation of the patient resulting from the insertion of the needle tip of the needle portion; and
compressing the bulb portion of the plungerless aspiration and/or injection device to inject the non-toxic dark nanoparticles or microparticles inside a desired part of a central cornea of the patient so as to create a 1-3 mm diameter darkened annular area, while leaving a 1-2 mm diameter central transparent area for light to pass through the central transparent area, which functions as a pinhole to treat presbyopia, myopia, and reduce astigmatic aberrations of the cornea.

11. The method according to claim 10, wherein the end portion of the housing is an inverted conical end portion or inverted frustoconical end portion; and
wherein the step of pressing the outer edge of the end portion of the housing against the body portion of the patient further comprises pressing the outer edge of the inverted conical end portion or inverted frustoconical end portion of the housing against the skin of the patient to numb the subcutaneous nerves prior to insertion of the needle tip of the needle portion into the skin of the patient so as to reduce a pain sensation of the patient resulting from the insertion of the needle tip of the needle portion.

12. The method according to claim 10, wherein the plungerless aspiration and/or injection device is configured for a single use on a patient; and wherein the method further comprises the step of:
disposing of the plungerless aspiration and/or injection device after injecting the non-toxic dark nanoparticles or microparticles inside the desired part of the central cornea of the patient.

13. A plungerless aspiration and/or injection device, comprising:
a housing, the housing including an end portion extending outwardly from the housing, the end portion having an outer edge that is configured to be pressed against a body portion of a patient, and the housing further including a graded flexible guard that indicates the amount of a fluid or medication that is injected in a body cavity;
a needle portion disposed in the housing, the needle portion including a needle tip, and the needle tip configured to be extended beyond the outer edge of the end portion of the housing; and
a bulb portion disposed in the housing, the bulb portion defining a fluid containing cavity that is fluidly coupled to the needle portion, and the bulb portion being elastically deformable so that the user is able to perform aspiration, injection, and/or implantation on the patient by manipulating the bulb portion;
wherein the outer edge of the end portion of the housing is configured to be pressed against the body portion of the patient prior to insertion of the needle tip of the needle portion into the body portion of the patient so as to reduce a pain sensation of the patient resulting from the insertion of the needle tip of the needle portion.

14. The plungerless aspiration and/or injection device according to claim 13, wherein the end portion of the housing is an inverted conical end portion or inverted frustoconical end portion.

15. The plungerless aspiration and/or injection device according to claim 13, wherein the housing comprises elastically deformable forked blades disposed over the bulb, the elastically deformable forked blades configured to be depressed by the user between a thumb and index finger of the user so as to controllably regulate a flow of fluid out of, or into the needle tip.

16. The plungerless aspiration and/or injection device according to claim 15, wherein the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

17. The plungerless aspiration and/or injection device according to claim 13, wherein the needle portion has a 19 gauge to 44 gauge needle diameter.

18. The plungerless aspiration and/or injection device according to claim 13, wherein the needle portion has a diameter between approximately 0.001 millimeters and approximately 1.0 millimeters.

19. The plungerless aspiration and/or injection device according to claim 13, wherein the needle portion has a needle length between approximately 1 millimeter and approximately 100 millimeters.

20. The plungerless aspiration and/or injection device according to claim 13, wherein the bulb portion is formed from a compressible silicone, rubber, or other elastic polymer.

* * * * *